(12) United States Patent
Dedig et al.

(10) Patent No.: US 7,691,085 B2
(45) Date of Patent: Apr. 6, 2010

(54) SYRINGE INTERFACES AND ADAPTERS FOR USE WITH MEDICAL INJECTORS

(75) Inventors: James Albert Dedig, Pittsburgh, PA (US); Frank A. Lazzaro, Pittsburgh, PA (US); Kevin P. Cowan, Allison Park, PA (US); Mark W. Hitchins, Sewickley, PA (US); Charles J. Mutschler, Wexford, PA (US); James R. Neill, Oakdale, PA (US)

(73) Assignee: Medrad, Inc., Indianola, PA (US)

( * ) Notice: Subject to any disclaimer, the term of this patent is extended or adjusted under 35 U.S.C. 154(b) by 1592 days.

(21) Appl. No.: 10/295,297

(22) Filed: Nov. 15, 2002

(65) Prior Publication Data

US 2003/0120212 A1 Jun. 26, 2003

Related U.S. Application Data

(63) Continuation-in-part of application No. PCT/US02/01658, filed on Jan. 18, 2002.

(60) Provisional application No. 60/262,521, filed on Jan. 18, 2001.

(51) Int. Cl.
*A61M 5/20* (2006.01)
(52) U.S. Cl. .................................. 604/151; 128/DIG. 1
(58) Field of Classification Search .................. 604/151; 128/DIG. 1
See application file for complete search history.

(56) References Cited

U.S. PATENT DOCUMENTS 4,006,736 A 2/1977 Kranys et al.

(Continued)

FOREIGN PATENT DOCUMENTS

EP 0 584 531 3/1994

(Continued)

OTHER PUBLICATIONS

US 3,694,139, 06/1976, Kleinmann et al. (withdrawn).

(Continued)

*Primary Examiner*—Nicholas A Lucchesi
*Assistant Examiner*—Laura A Bouchelle
(74) *Attorney, Agent, or Firm*—Jill Denesvich; Henry E. Bartony, Jr.

(57) ABSTRACT

A syringe interface includes a top opening into which a syringe can be loaded, a first retaining member positioned on one side of the opening and a second retaining member positioned on a second side of the opening. The first retaining member and the second retaining member abut a forward facing abutment surface of a syringe flange on the syringe generally symmetrically. The syringe interface further includes a cradle, at least one engagement member to abut a forward facing abutment surface of a syringe flange, and a carriage slidably disposed within the cradle. The carriage includes a connector to form a releasable connection with a plunger or plunger extension of the syringe and a drive member of the injector. The connector includes a plurality of flexing capture members that flex radially outward to connect to a flange on the rear of the plunger or plunger extension of the syringe when the carriage is moved forward within the syringe interface. The syringe interface may further include a connector on a rear portion thereof to connect to the injector.

25 Claims, 9 Drawing Sheets

U.S. PATENT DOCUMENTS

| | | | |
|---|---|---|---|
| 4,082,094 A | | 4/1978 | Dailey |
| 4,255,096 A | * | 3/1981 | Coker et al. ................. 417/415 |
| 4,608,042 A | * | 8/1986 | Vanderveen et al. .......... 604/81 |
| 4,677,980 A | | 7/1987 | Reilly et al. |
| 4,838,857 A | * | 6/1989 | Strowe et al. ................. 604/67 |
| 4,997,421 A | | 3/1991 | Palsrok et al. |
| 5,383,851 A | * | 1/1995 | McKinnon et al. ............ 604/68 |
| 5,383,858 A | | 1/1995 | Reilly et al. |
| 5,520,653 A | | 5/1996 | Reilly et al. |
| 5,865,805 A | | 2/1999 | Ziemba |
| 5,899,885 A | | 5/1999 | Reilly et al. |
| 5,944,694 A | | 8/1999 | Hitchins et al. |
| 6,312,410 B1 | | 11/2001 | Yamamoto |
| 6,428,509 B1 | * | 8/2002 | Fielder ....................... 604/154 |
| 7,018,363 B2 | | 3/2006 | Cowan et al. |
| 2001/0047153 A1 | | 11/2001 | Trocki et al. |
| 2004/0087909 A1 | | 5/2004 | Nemoto |

FOREIGN PATENT DOCUMENTS

| | | |
|---|---|---|
| EP | 0 919 251 | 6/1999 |
| EP | 1016427 A2 * | 7/2000 |
| EP | 1351730 | 6/2006 |
| WO | 8900866 | 2/1989 |
| WO | WO 92/21391 | 12/1992 |
| WO | 97/07838 | 3/1997 |
| WO | 97/36635 | 10/1997 |
| WO | 99/10032 | 3/1999 |
| WO | 01/08727 | 2/2001 |
| WO | 01/37903 | 5/2001 |

OTHER PUBLICATIONS

International Search Report for counterpart PCT Publication No. WO 02/056947.

International Preliminary Examination Report for counterpart PCT Publication No. WO 02/056947.

* cited by examiner

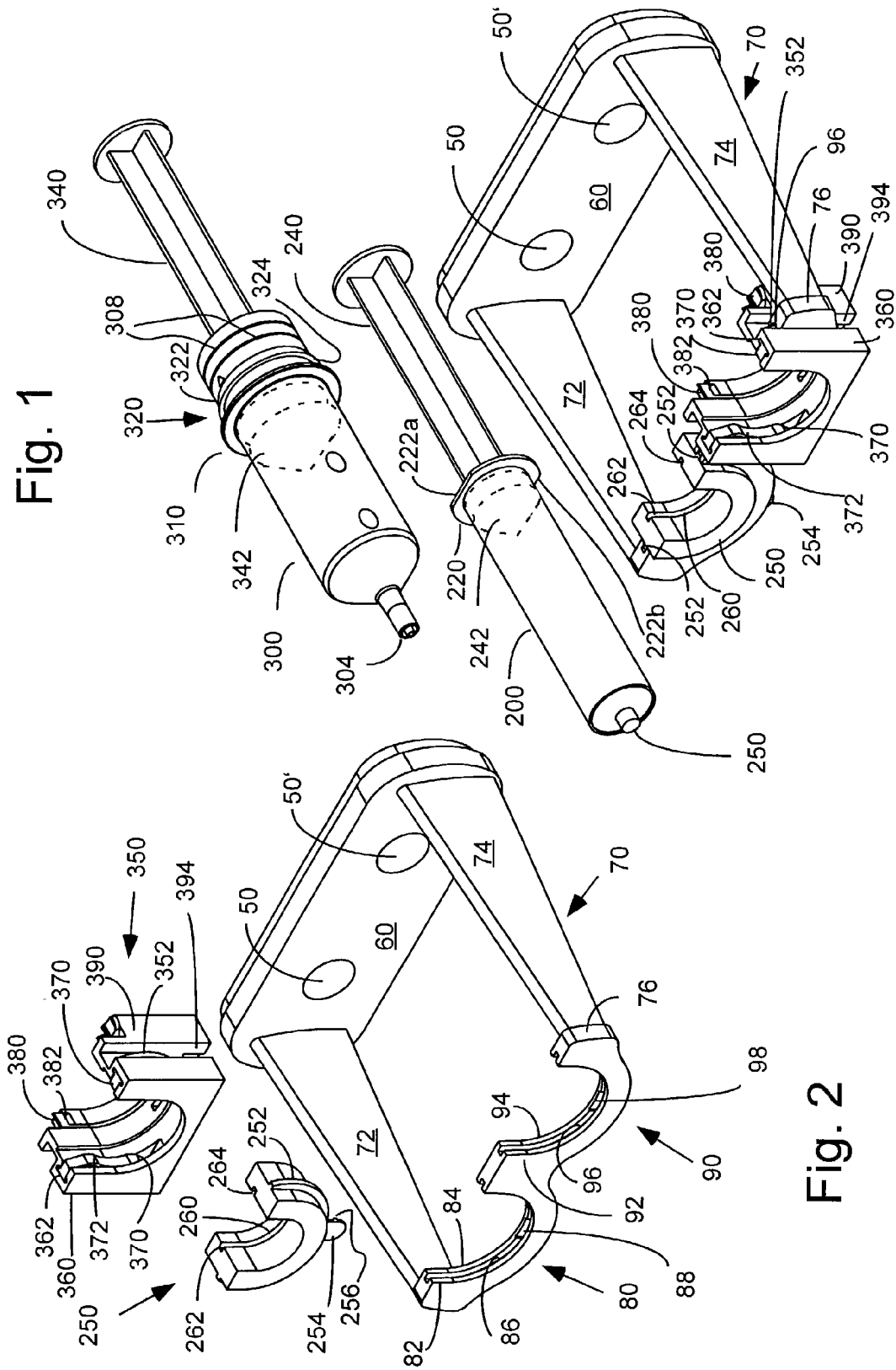

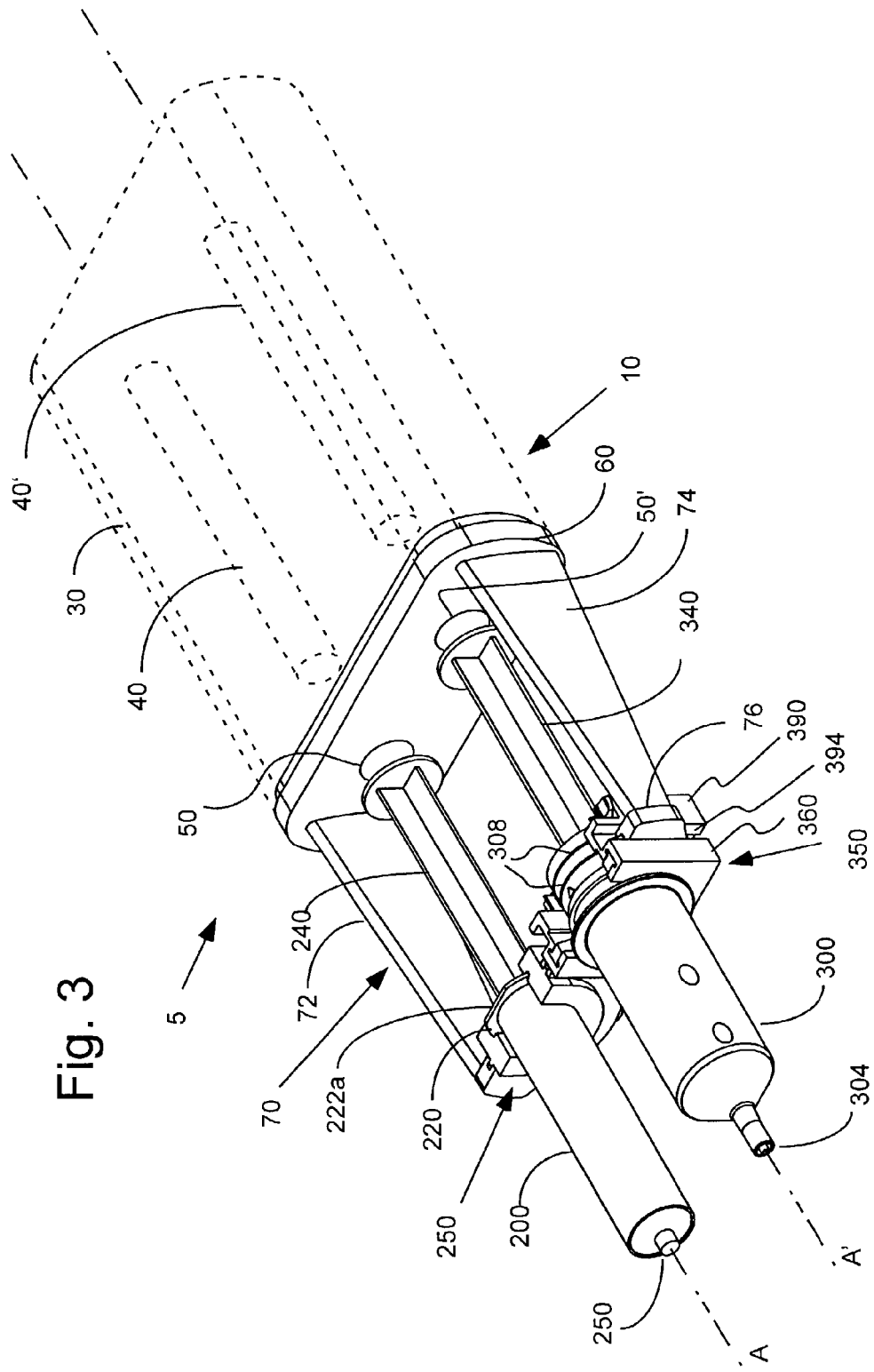

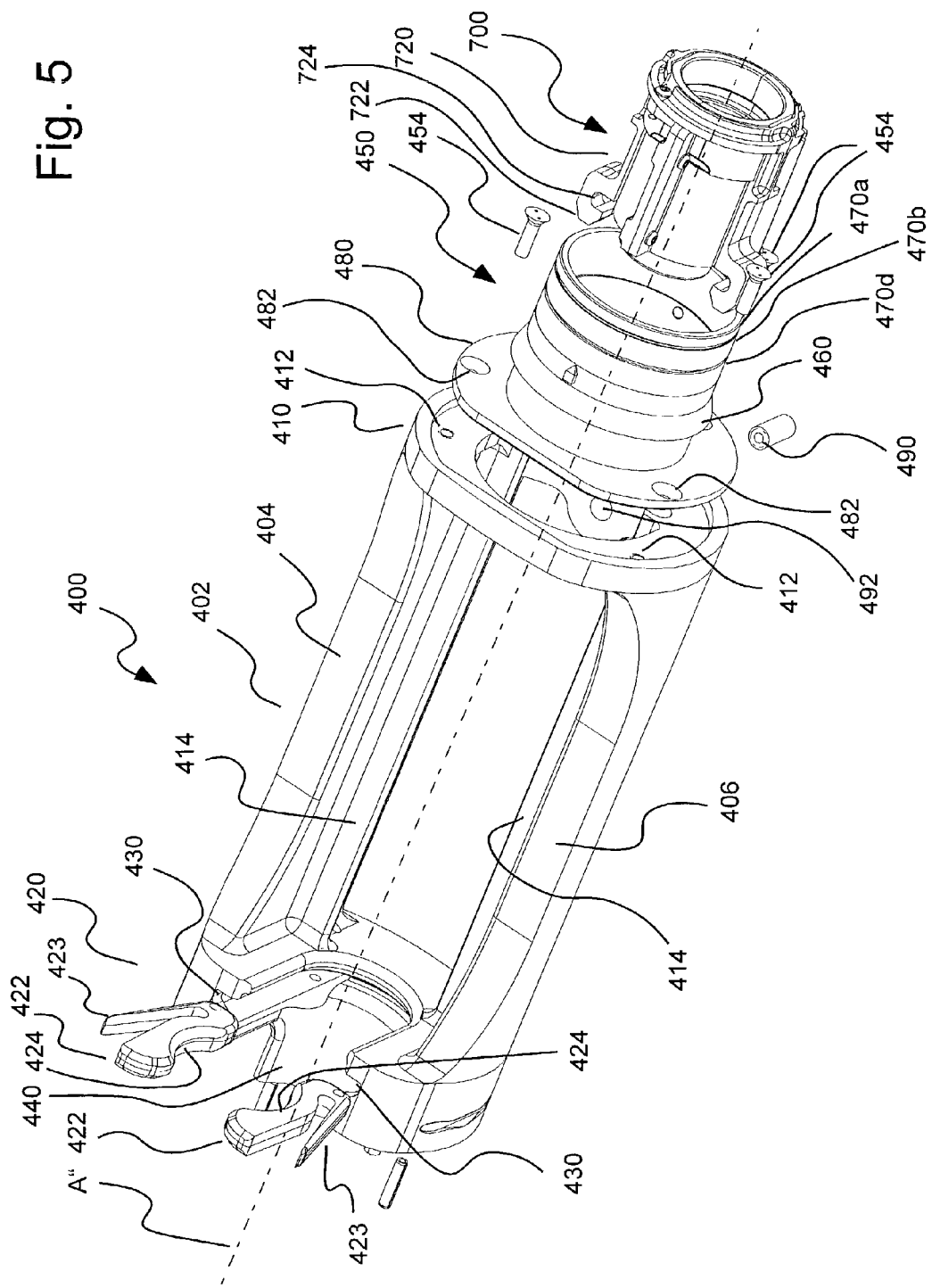

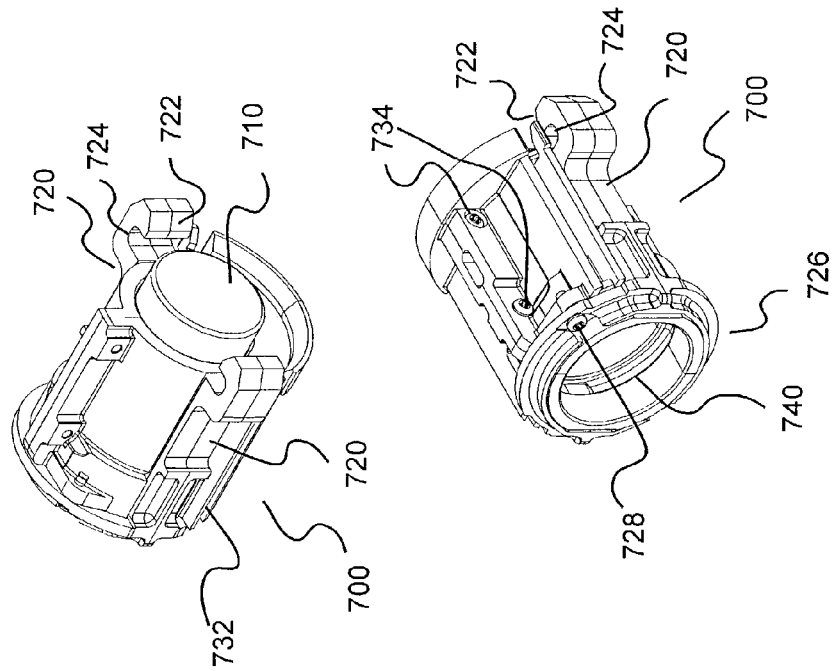
Fig. 6B
Fig. 6C
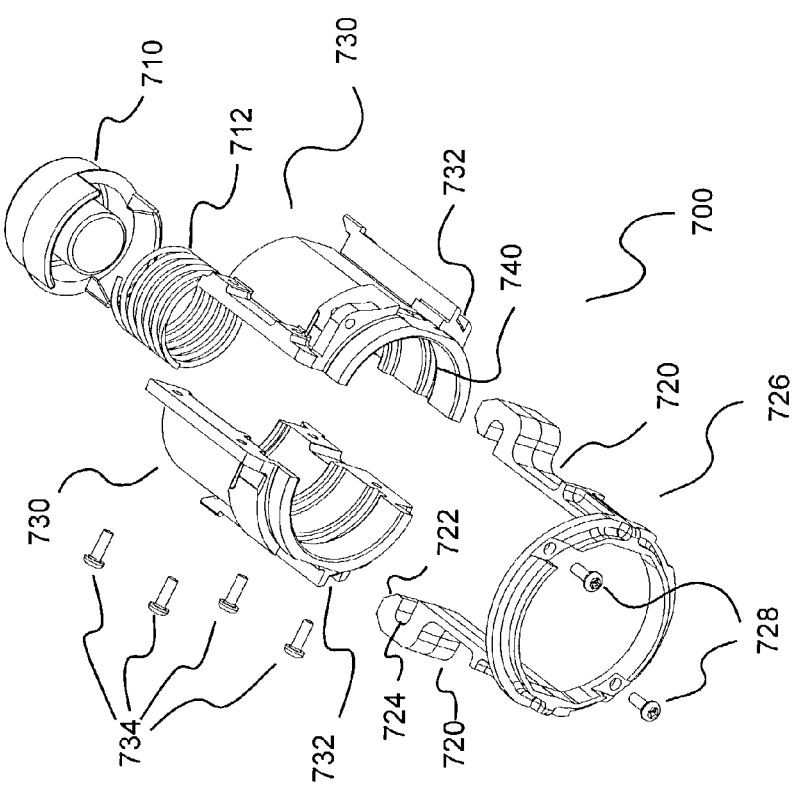
Fig. 6A

SYRINGE INTERFACES AND ADAPTERS FOR USE WITH MEDICAL INJECTORS

CROSS-REFERENCE TO RELATED APPLICATIONS

This application is a continuation in part of PCT International Patent Application Ser. No. PCT/US02/01658, filed Jan. 18, 2002 and designating the United States, which claims the priority of U.S. Provisional Patent Application Ser. No. 60/262,521, filed Jan. 18, 2001.

BACKGROUND OF THE INVENTION

The present invention relates generally to syringe interfaces and syringe adapters and, more particularly, to syringe interfaces and syringe adapters for use with medical injectors and to medical injector systems using such syringe interfaces and adapters.

A number of injector-actuated syringes and powered injectors for use in medical procedures such as angiography, computed tomography, ultrasound and NMR/MRI have been developed. U.S. Pat. No. 4,006,736, for example, discloses an injector and syringe for injecting fluid into the vascular system of a human being or an animal. Typically, such injectors comprise drive members such as pistons that connect to a syringe plunger. For example, U.S. Pat. No. 4,677,980, the disclosure of which is incorporated herein by reference, discloses an angiographic injector and syringe wherein the drive member of the injector can be connected to, or disconnected from, the syringe plunger at any point along the travel path of the plunger via a releasable mechanism. A front-loading syringe and injector system is also disclosed in U.S. Pat. No. 5,383,858, the disclosure of which is incorporated herein by reference.

The front-loading injector of U.S. Pat. No. 5,383,858 includes a mounting mechanism for securing the syringe to the front wall of the injector. Other types of mounting mechanisms for front-loading syringes are disclosed in PCT Publication No. WO 01/37903 and U.S. patent Application Publication No. 2001-47153, each assigned to the assignee of the present invention, the disclosures of which are incorporated herein by reference. The use of specifically designed mounting mechanisms generally prevents the use of syringes of other various types with front-loading injectors. Syringe adapters attachable to those front-loading injectors are sometimes used to allow the use of such syringes with the front-loading injectors.

For example, U.S. Pat. No. 5,520,653 discloses several adapters designed to allow the use of various syringes with a front-loading injector. In one embodiment, the adapter of U.S. Pat. No. 5,520,653 includes a syringe carrier having a front end, a rear end, and a syringe-retaining channel located between the carrier front and rear ends for engaging at least a portion of the syringe flange. Mounting flanges near the rearward end of the carrier releasably mount the carrier in a desired position relative to the front wall of the injector. Another adapter for allowing use of various syringes with a front-loading injector is disclosed in Japanese Patent Publication No. 09-122234. In this adapter, a pair of pinching elements rotates to contact a portion of a syringe flange to retain the syringe upon the adapter. Other adapters are disclosed in PCT Publication No. WO 01/08727 and U.S. patent application Ser. No. 09/633,299, filed on Aug. 8, 2000, each assigned to the assignee of the present invention, the disclosures of which are incorporated herein by reference.

Although a number of syringe interfaces and adapters are currently available, it remains desirable to develop improved syringe interfaces and adapters for use with syringes of various types to permit use of such syringes with injectors.

SUMMARY OF THE INVENTION

In general, the present invention provides syringe interfaces and adapters for removably or releasably attaching a syringe to an injector. The syringe interfaces or retaining members of the present invention can be permanently attached to an injector or can be attachable or removably attachable to an injector via an attachment mechanism (for example, to a different type of syringe interface on the injector). In the case that a syringe interface of the present invention is attachable to an injector, the syringe interface can be used as an adapter to attach a syringe to the injector that would otherwise be unusable with that injector.

In one aspect, the present invention provides a syringe interface to connect a syringe to an injector having a drive member. The syringe includes a radially extending flange with a forward facing abutment surface and a plunger disposed within the syringe. The syringe interface includes a top opening into which the syringe can be loaded, a first retaining member positioned on one side of the opening and a second retaining member positioned on a second side of the opening. The first retaining member and the second retaining member abut the forward facing abutment surface of the syringe flange generally symmetrically. In a further aspect, the syringe interface may include a connector on a rear portion thereof to connect to the injector, At least one of the first retaining member and the second retaining member can include a radially inward extending member that moves radially outward when contacted by the syringe during loading of the syringe into the interface and returns to a radially inward position once the syringe is loaded within the interface. In one embodiment, each of the first retaining member and the second retaining member include a radially inward extending member. The radially inward extending member(s) can return to a radially inward position after loading of the syringe in a manner that causes audible feedback to inform a user that the syringe is properly seated within the syringe adapter. The radially inward extending members can be biased by a biasing member (for example, a spring) or can be fabricated, at least in part, from a flexible or resilient material that flexes radially outward when contacted by the syringe.

The syringe interface can further include a carriage slidably connected therein including a plunger connector to form a releasable connection with the plunger of the syringe and the drive member of the powered injector. The carriage can, for example, slide within a cradle section of the interface. The plunger connector can, for example, include a plurality of flexing capture members that flex radially outward to connect to a flange on the rear of the plunger of the syringe when the carriage is moved forward within the syringe interface. The carriage can further include a drive member connector to form a releasable connection with the drive member. For example, the drive member connector can include at least one abutment flange to form an abutting connection with at least one radially projecting member of the drive member. Preferably, the drive member connector can be connected to the drive member regardless of the orientation of the carriage about its axis relative to the drive member.

In another aspect, the present invention provides a syringe adapter to connect a syringe to a powered injector having a drive member. As described above, the syringe includes a radially extending flange with a forward facing abutment surface, a plunger disposed within the syringe and a plunger extension projecting rearward from the syringe. The adapter includes an injector connector on a rear portion of the adapter to connect the adapter to the powered injector, a cradle extending forward from the injector connector; a syringe interface to abut the forward facing abutment surface of the syringe flange, and a carriage slidably disposed within the cradle. The carriage includes a plunger extension connector to form a releasable connection with the plunger extension of the syringe and the drive member of the powered injector. The plunger extension connector can include a plurality of flexing capture members that flex radially outward to connect to a flange on the rear of the plunger extension of the syringe when the carriage is moved forward within the syringe adapter.

In a further aspect, the present invention provides injector systems including an injector and a syringe adapter or a syringe interface as described above, and methods for attaching syringes to a syringe adapter or a syringe interface.

In another aspect, the present invention provides a syringe adapter for use with a syringe that includes a radially extending flange with a forward facing abutment surface. The adapter includes a top opening into which the syringe can be loaded. A first retaining member is preferably positioned on one side of the opening and a second retaining member is preferably positioned on a second side of the opening. The first retaining member and the second retaining member abut the forward facing abutment surface of the syringe flange in a generally symmetrical manner so that bending moments on the syringe are reduced or even substantially eliminated.

At least one of the first retaining member and the second retaining member preferably includes a flexible, radially inward extending member that flexes radially outward when contacted by the syringe during loading of the syringe into the adapter and returns to a radially inward position once the syringe is loaded within the adapter. More preferably, the first retaining member and the second retaining member include a flexible, radially inward extending member that flexes radially outward when contacted by the syringe during loading of the syringe into the adapter and returns to a radially inward position once the syringe is loaded within the adapter. The return of the extending member(s) to the radially inward position preferably causes feedback (for example, audible feedback) to a user to let the user know the syringe is properly seated within the syringe adapter.

The syringe interfaces or adapters can also include an additional or a third retaining member positioned to the rear of the first retaining member and the second retaining member, which preferably has generally the same shape as the rearward end of the syringe. The third retaining member is preferably adapted to abut the rearward end of the syringe after the syringe has been loaded into the syringe interface or adapter and the third retaining member has been placed in a closed position. The third retaining member reduces distortion of the shape of the syringe that can occur during an injection procedure.

In another aspect, the present invention provides an injector system including an injector and at least a first syringe. The powered injector includes at least a first drive member for pressurizing a fluid within a first syringe and a cradle extending forward of a first opening in the injector through which the drive member communicates with the interior of the first syringe. The cradle includes at least a first syringe adapter retention mechanism on a forward end of the cradle. The injector system further includes at least a first adapter for attaching the first syringe to the injector. The first adapter includes a releasable attachment mechanism for releasably attaching the first adapter to the first adapter retention mechanism. The first adapter also includes a top opening into which the syringe can be loaded. A first retaining member is preferably positioned on one side of the opening and a second retaining member is preferably positioned on a second side of the opening as described above. The first retaining member and the second retaining member abut the forward facing abutment surface of the syringe flange in a generally symmetrical manner when the first syringe is loaded so that bending moments on the first syringe are reduced or, preferably, substantially eliminated.

One or both of the first retaining member and the second retaining member preferably includes a radially inward extending member that moves radially outward when contacted by the first syringe during loading of the first syringe into the adapter and returns to a radially inward position once the first syringe is loaded within the adapter. As discussed above, the radially inward extending member(s) preferably return(s) to a radially inward position after loading of the syringe in a manner which causes feedback (for example, audible feedback) to a user to let the user know the syringe is properly seated within the syringe adapter. The adapter can also include a third retaining member positioned to the rear of the first retaining member and the second retaining member to reduce or to substantially eliminate distortion of the shape of the syringe during an injection procedure.

In still another aspect, the present invention provides a syringe interface for connecting a syringe comprising a flange with a forward facing abutment surface and a plunger movably disposed therein to an injector comprising a drive member. The syringe interface includes a cradle member; at least one engagement member adapted to abut the forward facing abutment surface of the syringe flange; a support attached to the engagement member and extending forward; a heater attached to the support to contact the syringe to transfer heat energy to the contents of the syringe; and a carriage slidably disposed within the cradle. The carriage includes a plunger connector to form a releasable connection with the syringe plunger and the drive member of the injector. The support can include a passage therein through which force can be applied to the barrel of the syringe to assist in removing the syringe from the syringe interface. The syringe interface preferably further includes an injector connector on a rear portion thereof to connect the syringe interface to the injector.

The engagement member can include at least one radially inward extending retaining member that moves radially outward when contacted by the syringe during loading of the syringe into the syringe interface and returns to a radially inward position once the syringe is loaded within the syringe interface. As described above, the retaining member can formed of a flexible or resilient material or can be biased by a biasing element.

In one embodiment, the heater comprise two heating elements that contact a barrel of the syringe an opposing sides thereof. The heating element or elements can move radially outward when contacted by the syringe during loading of the syringe into the syringe interface and return to a radially inward position once the syringe is loaded within the syringe interface. Preferably, the heating element(s) conform generally to the shape of the syringe barrel.

The present invention also provides in another aspect, an injector system including an injector and the syringe interface described above. Likewise, the present invention provides a method of attaching a syringe comprising a flange and a plunger movably disposed therein to the syringe interface described above including the steps of: loading the syringe into a top opening of the syringe interface; engaging the syringe flange with the engagement member of the syringe interface; and engaging a barrel of the syringe with the heater.

In still a further aspect, the present invention provides a syringe interface for connecting a syringe to an injector including a drive member, the syringe interface includes: an injector connector on a rear portion of the syringe interface to connect the syringe interface to an injector; at least one engagement member adapted to abut the syringe and retain the syringe in connection with the adapter when under axial loading from the injector; a support attached forward to the engagement member and extending forward; and a heater attached to the support to contact the syringe to transfer heat energy to the contents of the syringe. The support can include a passage therein through which force can be applied to the barrel of the syringe to assist in removing the syringe from the syringe interface.

BRIEF DESCRIPTION OF THE DRAWINGS

Other aspects of the invention and their advantages will be discerned from the following detailed description when read in connection with the accompanying drawings, in which:

FIG. 1 illustrates a perspective view of an embodiment of a front portion of an injector including a syringe cradle with two syringe adapters.

FIG. 2 illustrates a perspective view of the injector front portion of FIG. 1 in which the syringe adapters are in a disconnected state.

FIG. 3 illustrates a perspective view of the injector of FIG. 1 in which the adapters have been connected to the syringe cradle and the syringes have been loaded within the adapters.

FIG. 5 illustrates a perspective view of an embodiment of an adapter for attaching a syringe cradle having a syringe connector or adapter on a front end thereof to a front-loading injector FIG. 6A illustrates the plunger extension carriage of the adapter of FIG. 5 in a disassembled or exploded state.

FIG. 6B illustrates a front perspective view of the plunger extension carriage of FIG. 5.

FIG. 6C illustrates a rear perspective view of the plunger extension carriage of FIG. 5.

DETAILED DESCRIPTION OF THE INVENTION

Figure 4:
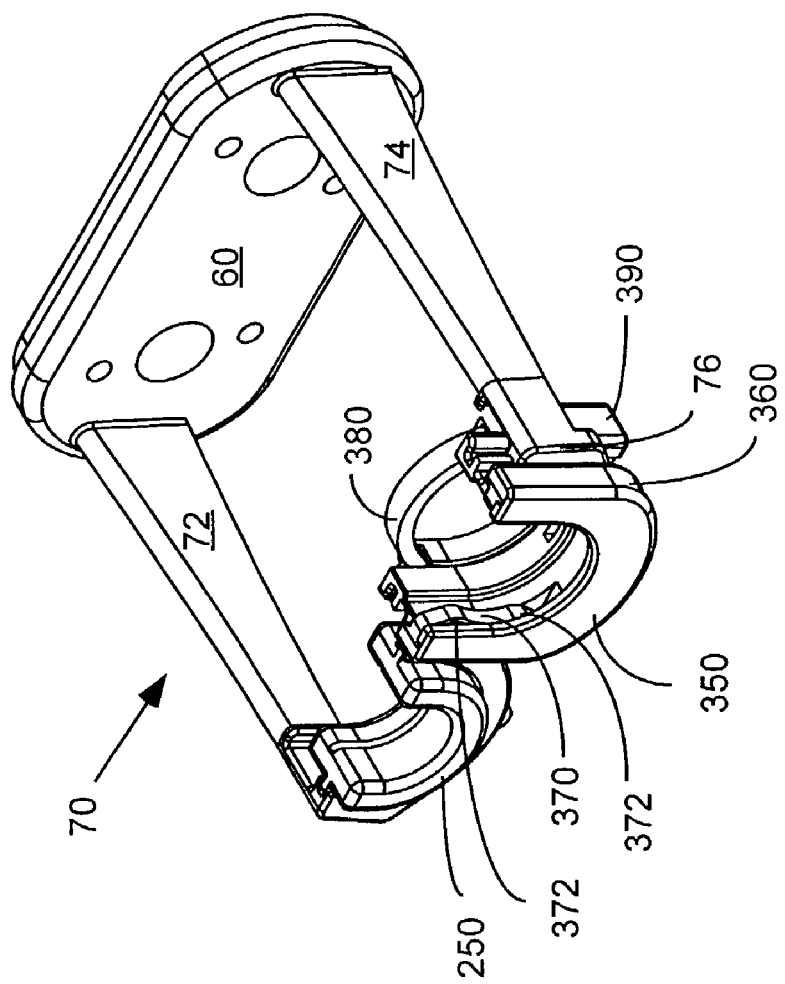
FIG. 4 illustrates a perspective view of the injector front portion of FIG. 1 in which the adapters have been connected to the syringe cradle and a rotating retaining member in one of the adapter is in a closed position.

An embodiment of a front-loading injector system 5 (see, for example, FIG. 3) of the present invention is illustrated in FIGS. 1 through 4. Injector system 5 includes a powered injector 10 and syringes 200 and 300 for injection of, for example, a contrast medium and/or saline. As best illustrated in FIG. 3, injector housing 30 of injector 10 preferably includes therein a first powered drive member or piston 40 and a second powered drive member or piston 40' which, for example, cooperate with syringe plunger extensions or pushrods 240 and 340 (via passages 50 and 50', respectively, formed in injector face plate 60) to control the movement of plungers 242 and 342 slideably disposed in syringes 200 and 300, respectively, to inject a fluid from the interior of syringes 200 and 300 into a patient.

As used herein to describe injection system 5 and other embodiments of the present invention, the terms "axial" or "axially" refer generally to, for example, axis A and generally parallel axis A' (see FIG. 3) around which syringe 200 and piston 40 and syringe 300 and piston 40', respectively, are preferably formed (although not necessarily symmetrically therearound) and to directions collinear with or parallel to axis A or axis A'. The terms "proximal" or "rearward" refer generally to an axial or a longitudinal direction toward the end of injector housing 30 opposite the end to which syringes 200 and 300 are mounted. The terms "distal" or "forward" refer generally to an axial or a longitudinal direction toward a syringe tip 250 or syringe tip 304 (from which pressurized fluid exits syringes 200 and 300, respectively). The term "radial" refers generally to a direction normal to an axis such as axis A or axis A'.

A syringe cradle 70 is preferably attached to a forward portion or surface of faceplate 60. Syringe cradle 70 provides space for attachment of syringes such as syringes 200 and 300 including extending plunger pushrods or plunger extensions 240 and 340, respectively, to injector 10. In that regard, syringe cradle 70 includes two generally axially-oriented, members 72 and 74 which are connected via a transverse member 76 oriented generally perpendicular to axis A and axis A'. Transverse member 76 includes a first syringe adapter retainer 80 and a second syringe adapter retainer 90 adapted to accept syringe adapters 250 and 350, respectively. Preferably, retainers 80 and 90 are formed to be generally the same so that various syringe adapters can be used therewith interchangeably.

In the embodiment of FIGS. 1-4, retainer 80 includes a first generally U-shaped flange 82 and a second generally U-shaped flange 84 spaced to form a generally U-shaped slot 86 therebetween. U-shaped slot 86 is open on the top thereof. Likewise, retainer 90 includes a first generally U-shaped flange 92 and a second generally U-shaped flange 94 spaced to form a generally U-shaped slot 96 therebetween. U-shaped slot 96 is also open on the top thereof. Adapters 250 and 350 are provided with generally U-shaped flanges 252 and 352, respectively, to cooperate with slots 86 and/or 96 to connect adapters 250 and 350 to either one of retainers 80 or 90 as best illustrated in FIGS. 2 and 3.

As clear to one skilled in the art, many other cooperating attachment members on retainers 80 and 90 and adapters 250 and 350 are suitable for use in the present invention. Adapters 250 and 350 can also include a tab such as tab 254 of adapter 250 to cooperate with one of passages 88 or 98 formed in retainers 80 and 90, respectively, to secure the adapter within the retainer. Flexing tab 254 can, for example, include an extending flange 256 that cooperates with a radially outward or downward surface of flange 84 of retainer 80 to releasably retain adapter 250 within retainer 80.

Syringe 200 includes a rearward flange 220 having a partially circular shape with straight or flattened sides or flats 222*a* and 222*b* that are generally opposing and parallel. Rear mounting flange 220 of syringe 200 is of a thickness (or axial width) that is slightly less than the axial width of a slot 260 formed in adapter 250. In one embodiment, the diameter of the circular part of flange 220 is a certain diameter and flats 222a and 222b are spaced a certain distance apart such that syringe 200 can be loaded radially (from the top) into slot 260 only when flats 222a and 222b are aligned with generally flat side portions 262 and 264 of the top opening of slot 260. In that regard, the radius of the generally circular portion of flange 220 is greater than the distance between flats 222a and 222b. The width of the opening of slot 260 is preferably slightly greater than distance between flats 222a and 222b. Slot 260 is dimensioned so that once syringe flange 220 is inserted fully therein, syringe 200 can be rotated about its axis so that flats 222a and 222b on syringe flange 220 are no longer aligned with the opening of slot 260 as illustrated in FIG. 3. When rotated to this position, syringe 200 cannot be removed because the circular part of syringe flange 220 cannot clear the opening of slot 260. To remove syringe 200, syringe 200 must be rotated about its axis so that flats 222a and 222b are once again aligned with side portions 262 and 264 of the opening of slot 260.

Syringe 300 is attached to syringe cradle 70 via adapter 350. In the embodiment of FIGS. 1 through 4, syringe 300 includes a radially extending, circumferential flange 310 on a rearward portion thereof. To the rear of flange 310, syringe 300 includes another circumferential flange 320 extending radially outward. Flange 320 includes a sloped surface 322 and an abutment shoulder 324. Syringe 300 is loaded radially (from the top) within adapter 350 such that the rear surface of flange 310 is forward of and abuts a forward surface of a forward portion 360 of syringe adapter 350, thereby preventing rearward axial motion of syringe 300. Syringe adapter 350 preferably contains at least one retaining element that can, for example, bias against syringe 300.

In the embodiment of FIGS. 1-4, syringe adapter 350 includes two flexible retaining elements 370 disposed within grooves or slots 362 on each lateral side of forward portion 360 of syringe adapter 350. Flexible retaining elements 370 can, for example, be formed from a resilient polymeric material such as an acetyl homopolymer (for example, DELRIN® available from DuPont). Flexible retaining elements 370 permit syringe 300 to be loaded radially into syringe adapter 350 by flexing radially outward and snapping back into place after syringe 300 has been loaded. Preferably, flexible retaining elements snap back into place with sufficient force to provide audible feedback to a user that syringe 300 has been properly and/or fully seated within syringe adapters 350. Other type of feedback such as tactile or visual feedback can be additionally or alternatively provided.

Syringe 300 is essentially constrained in the radial direction and the axial direction by the flexible retaining elements 370. In that regard, flexible retaining elements 370 rest between flange 310 and flange 320 of syringe 300 such that shoulder 324 abuts a rearward surface of inward extending portions 372 of flexible retaining elements 370, preventing forward axial motion of syringe 300. Preferably, flange 320 of syringe 300 abuts only the rearward surface of inward extending portions 372. Inward extending portions 372 can be formed to generally the shape of the barrel of syringe 300 (that is, generally in the shape of a cylinder). Inward extending portions 372 are preferably positioned symmetrically around syringe adapter 350 in a manner that their contact with flange 320 is symmetrical. Generally symmetrical loading of flange 320 or other abutment surface on syringe 300 reduces or prevents bending moments on syringe 300. Flexible retaining members as described above can also be used in connection with syringe adapter 250.

Although contact of syringe adapter 350 with symmetrically positioned areas or portions of syringe flange 320 reduces or prevents bending moments about syringe 300 as described above, contact at only limited portions of flange 320 can result in syringe distortion (for example, becoming oval in shape rather than round or cylindrical) in the case of certain syringes/syringe materials, particularly under high pressures. To prevent the rearward end of syringe 300 from deforming during high-pressure injection procedures, a second retaining element 380 can be moved into place around rearward end of syringe 300 after it is inserted into adapter 350 (see, for example, FIG. 4). In the embodiment of FIGS. 1-4, retaining element 380 is arced in shape to preferably closely match the arced or cylindrical shape of the rearward end of syringe 300. Retaining element 380 can, for example, be rotatably seated in an arced passage 382 formed in a rearward portion 390 of adapter 350 so that it can be rotated to surround the rearward end of syringe 300 when in the position illustrated in FIG. 4. Preferably, retaining element 380 closely abuts the rearward portion of syringe 300 around the upper circumference of the rearward end of syringe 300 to reduce or prevent distortion of the generally cylindrical shape of syringe 300 under high pressures.

Forward portion 360 and rearward portion 390 of syringe adapter 350 can, for example, form a generally U-shaped gap or slot 394 around the perimeter of syringe adapter 350 from which flange 352 projects radially outward. During attachment of syringe adapter 350 to retainer 90, slot 394 encompasses flanges 94 and 92 of retainer 90 while flange 352 seats in slot 96 to further secure the attachment of syringe adapter 350 to transverse member 76.

Adapters for use with cradle 70 of the present invention allow the use of many different types of syringes originally designed for manual injections or injections using a wide variety of powered injectors. Flange 320 of syringe 300 described above, for example, is designed to cooperate with a front-loading injector and release mechanism as described, in at least one embodiment, in PCT Publication No. WO 01/37903 and U.S. patent Application Publication No. 2001-47153, each assigned to the assignee of the present invention, the disclosures of which are incorporated herein by reference.

The rearward end of syringe 300 includes indicators 308 that can cooperate with a light source and sensors (see, for example, FIG. 7) to provide information about the configuration of syringe 300, as described in U.S. patent application Ser. No. 09/796,498, filed on Jan. 18, 2001, assigned to the assignee of the present invention, the disclosure of which is incorporated herein by reference.

Figure 7:
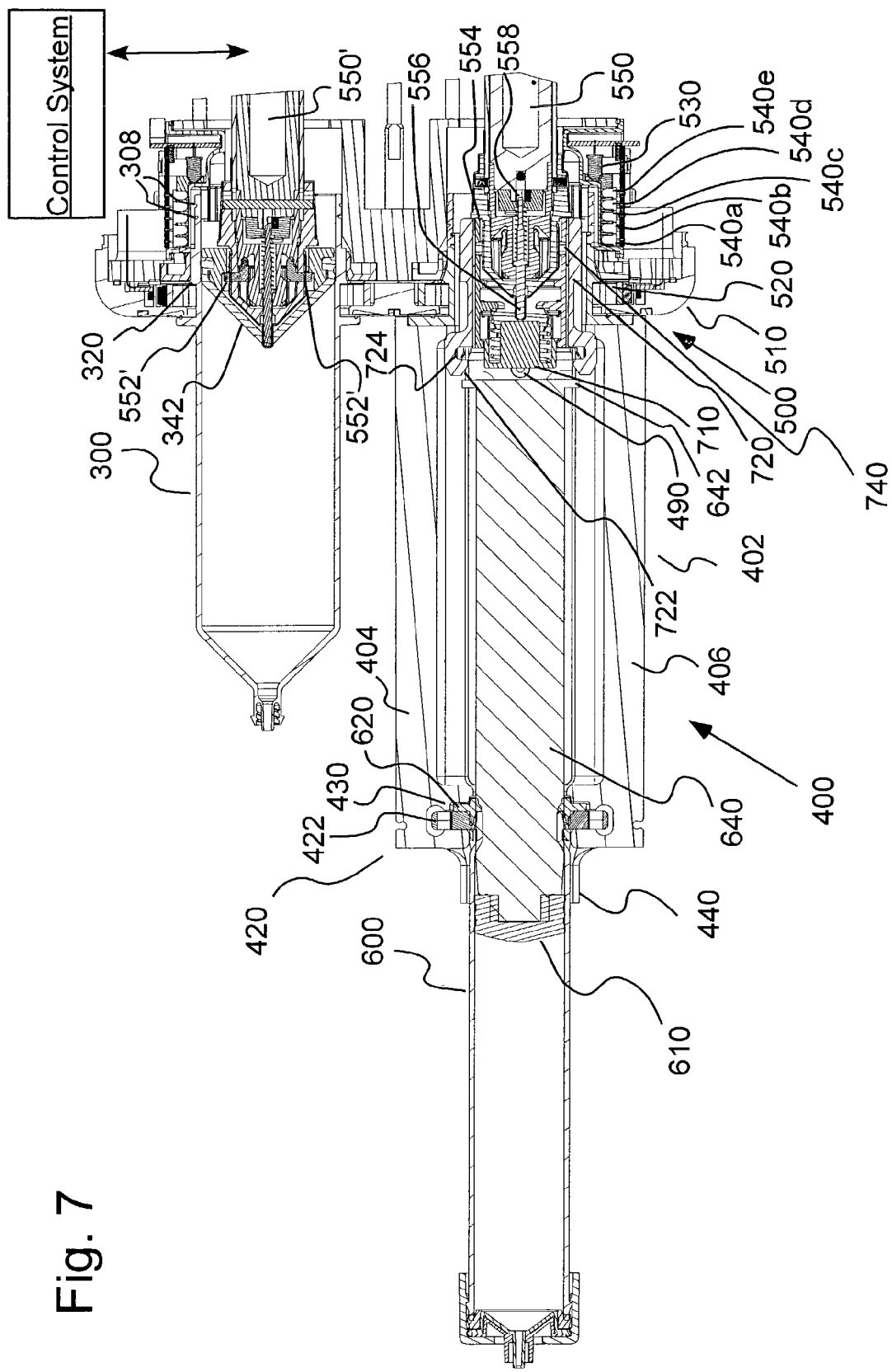
FIG. 7 illustrates a top, cross-sectional view of the adapter of FIG. 5 and a syringe attached to a front-loading injector.
Figure 8A:
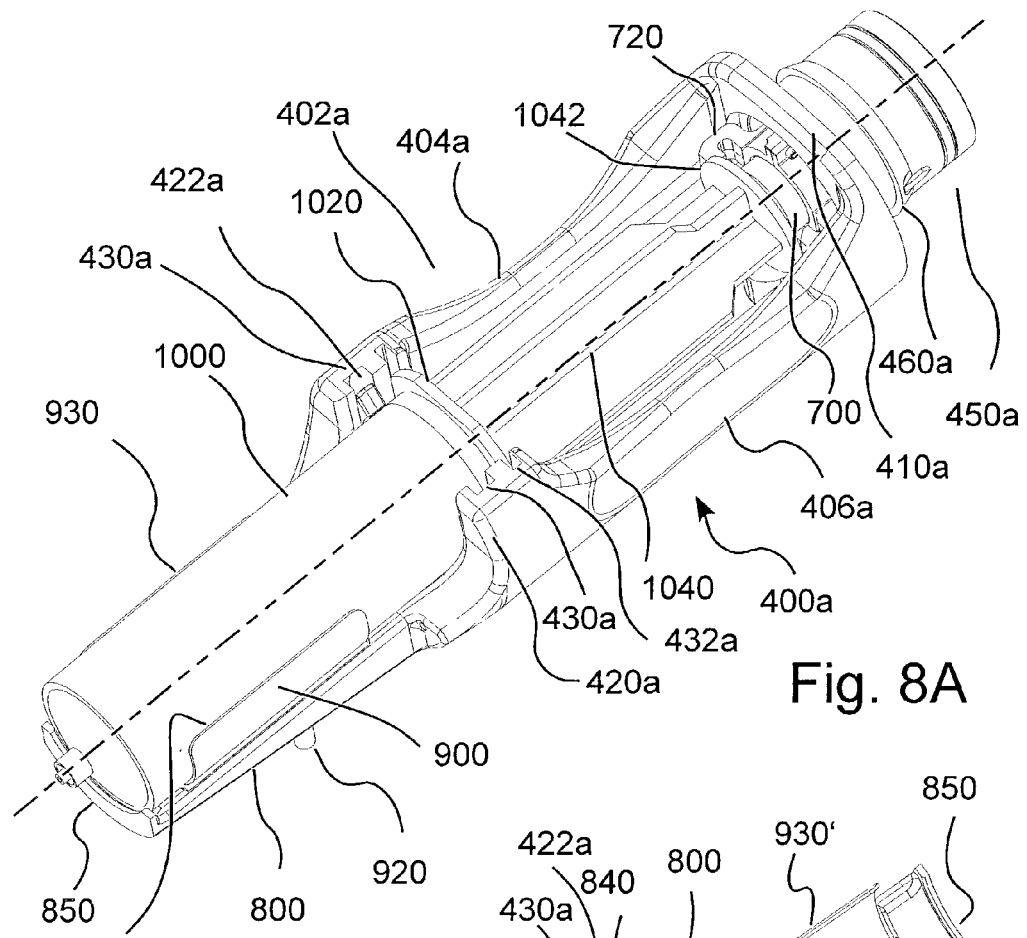
FIG. 8A illustrates a perspective view of the upper side of another embodiment of an adapter of the present invention with a syringe attached to the adapter.
Figure 8C:
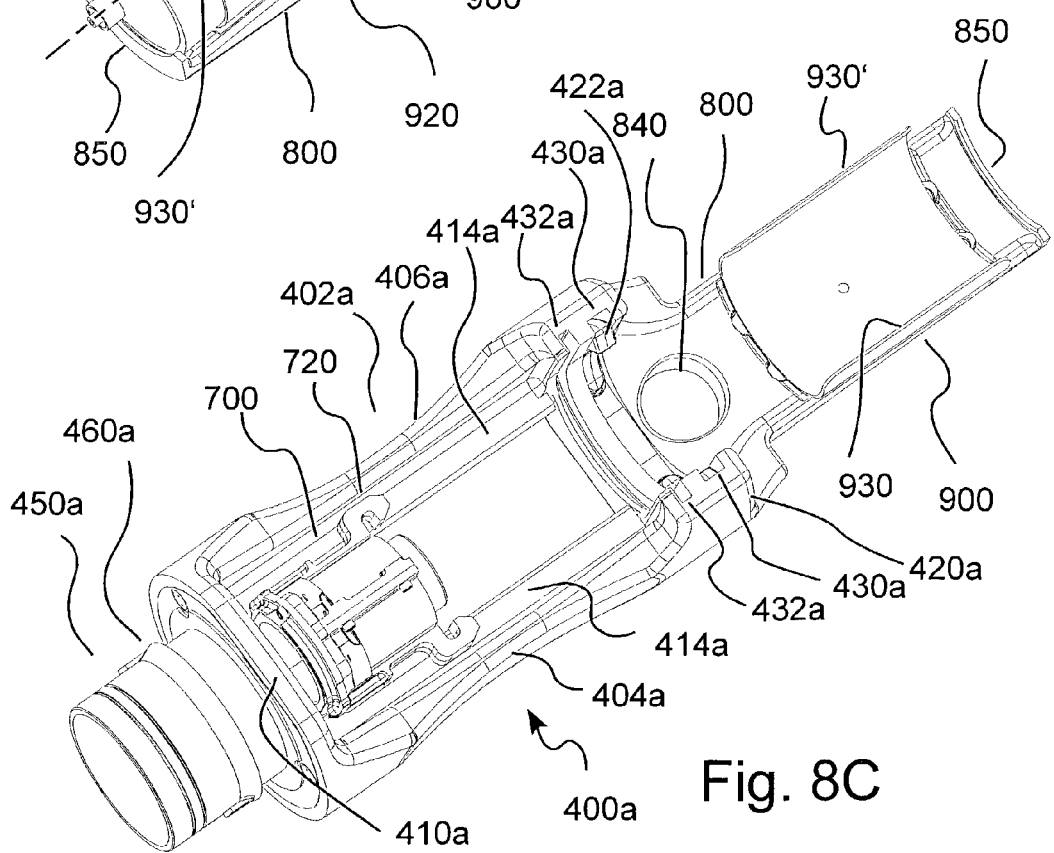
FIG. 8C illustrates another perspective view of the upper side of the adapter of FIG. 8A without a syringe attached to the adapter.
Figure 8B:
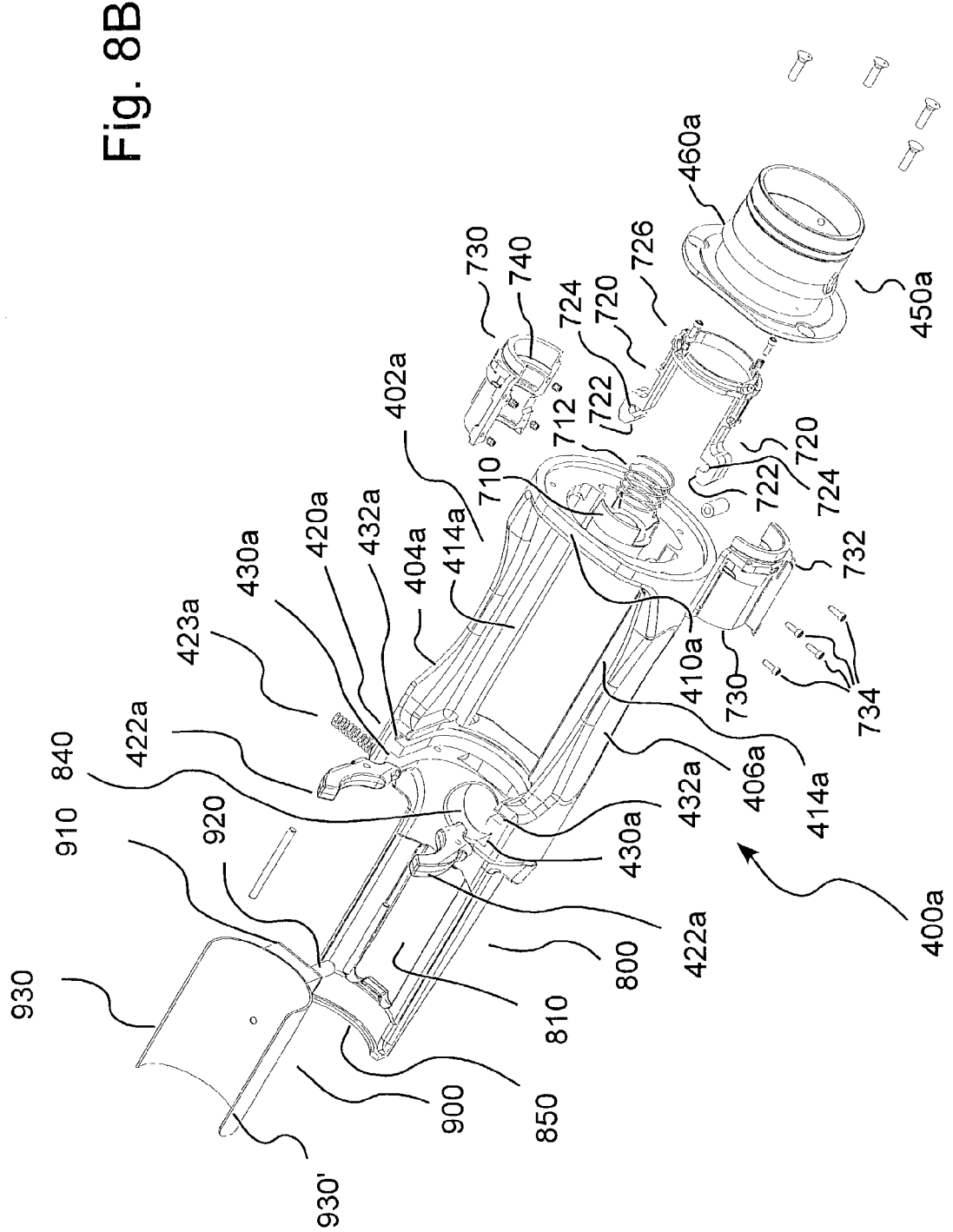
FIG. 8B illustrates an exploded view of the adapter of FIG. 8A.
Figure 8D:
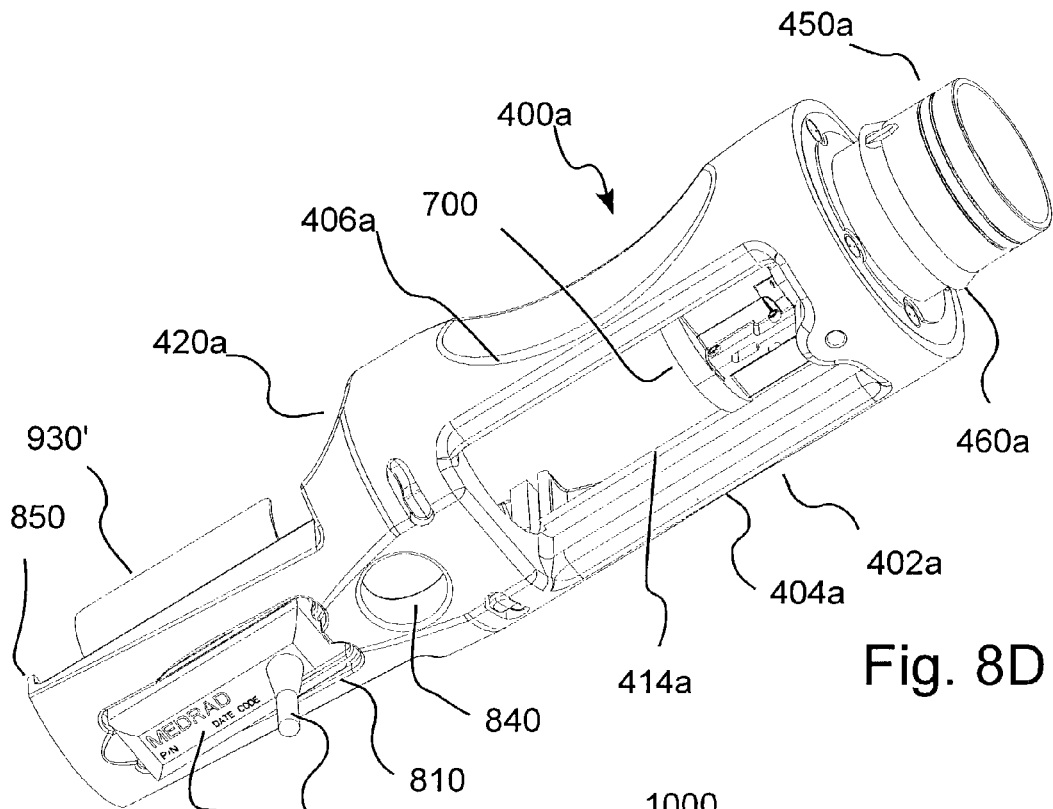
FIG. 8D illustrates a perspective view of the lower side of the adapter of FIG. 8A without a syringe attached to the adapter.
Figure 8E:
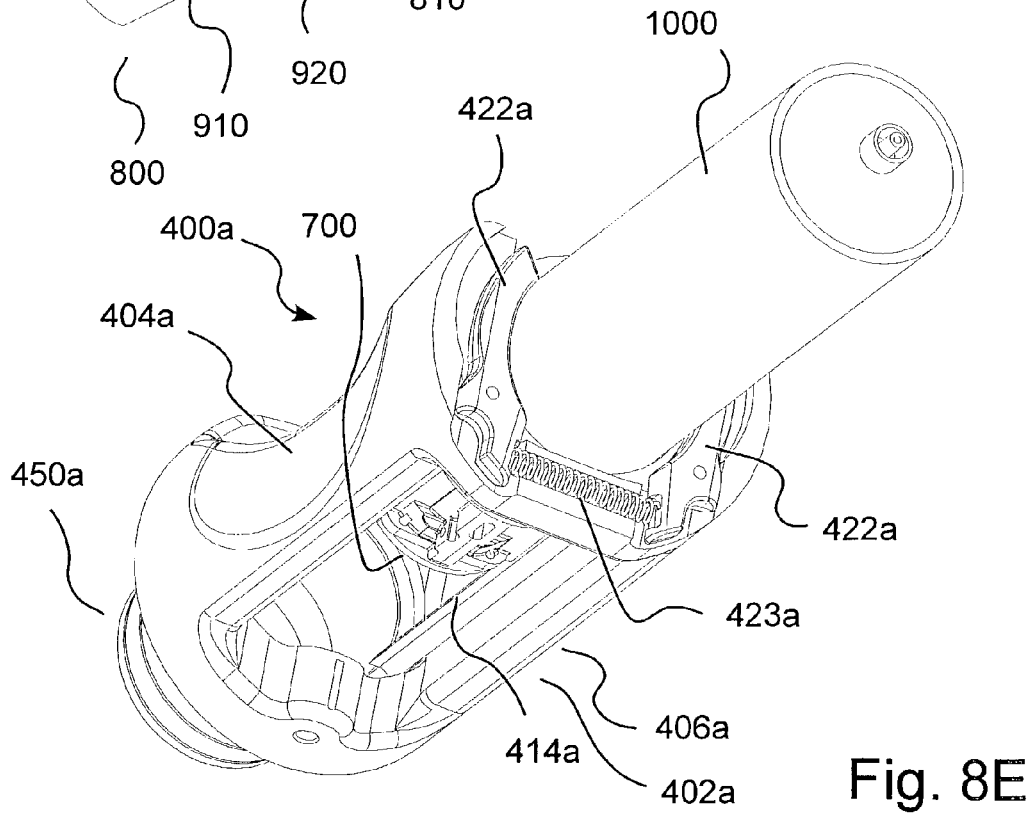
FIG. 8E illustrates a cutaway, perspective view of the lower side of the adapter of FIG. 8A with a syringe attached thereto.

FIGS. 5-7 illustrate another aspect of the present invention in which an adapter 400 including a single-syringe cradle 402 is attached to, for example, a dual-syringe injector 500 (see, FIG. 7) via a rear adapter or connector section 450. Syringe cradle 402 provides space for attachment of syringes such as, for example, syringes 200 and 600 including extending plunger pushrods 240 and 640, respectively, to injector 500. Syringe cradle 400 includes two generally, axially-oriented, members 404 and 406 which are connected at the rear thereof via a rear transverse member 410 oriented generally perpendicular to axis A" (see, for example, FIG. 5).

Adapter or connector 450 includes a flange 460 that operates similar in manner to flange 320 of syringe 300 described above to cooperate with front-loading injector 500 (as described in PCT Publication No. WO 01/37903 and U.S. patent Application Publication No. 2001-47153) to removably connect adapter 400 to injector 500. In that regard, flange 460 cooperates with a syringe interface 510 including a flex ring 520 that forms an abutting connection with flange 460 as illustrated in FIG. 7.

Adapter 450 can be removably attachable to transverse member 410 via the cooperation of one or more fasteners 454 (for example, screws) with holes or passages 482 and 412 formed in adapter 450 and transverse member 410, respectively. As clear to one skilled in the art, many different types of adapters or connectors other than adapter section 450 can be used to attach syringe cradle 402 to any number of different injectors having different syringe interfaces. Making adapter section 450 removably attachable to syringe cradle 402 can facilitate interchange of different injector adapter or connector sections with a single syringe cradle.

Adapter section 450 preferably further includes indicators such as grooved rings 470a, 470b and 470d that can cooperate with a light source 530 and sensors 540a, 540b and 540d of sensors 540a-e to provide information (via, for example, a binary code) about the configuration of adapter 450, as more fully described in U.S. patent application Ser. No. 09/796, 498. Via indicators 470a, 470b and 470d, the control system of injector 500 can be informed or alerted that adapter 400 is connected thereto and the operation of injector 500 can be controlled accordingly.

Adapter 400 further includes a syringe interface or adapter 420 at a forward end thereof between axially extending members 404 and 406. Syringe adapter or interface 420 can be made removable/interchangeable as described above for syringe adapters 250 and 350. Syringe interface 420 is permanently affixed to adapter 400 in the embodiments of FIGS. 5-7. Different syringe interfaces can be attached to injector 500 by removing adapter 400 and attaching another adapter with a different syringe interface or adapter.

Syringe interface 420 preferably includes at least one retaining element that can, for example, bias against syringe 600. In the embodiment of FIGS. 5-7, syringe interface 420 includes two flexible retaining elements 422 (for example, formed from a resilient polymeric material such as DELRIN) disposed within grooves or slots 430 on each lateral side of syringe interface 420. Flexible retaining elements 422 are shown disassembled in FIG. 5. Flexible retaining elements 422 permit syringe 600 to be loaded radially from above into syringe interface 420 by flexing radially outward and snapping back into place after syringe 600 has been loaded via spring lever elements 423 (see FIG. 5), much as described for syringe adapter 350 above. Preferably, flexible retaining elements 422 snap back into place with sufficient force to provide audible feedback to a user that syringe 600 has been properly and/or fully seated within syringe interface 420. Other type of feedback such as tactile or visual feedback can be additionally or alternatively provided. Syringe interface 420 also can include a forward syringe support 440 to abut a lower portion of syringe 600 to assist in preventing tilting or rotation of syringe 600 out of the plane of injector 500.

Syringe 600 is constrained in the radial direction and the axial direction by the flexing retaining elements 422. In that regard, after syringe 600 is lowered into adapter 400, flexible retaining elements 422 rest in slot 430 to the front of syringe flange 620 which abuts a rearward surface of flexing retaining elements 422, preventing forward axial motion of syringe 600. Inward surfaces 424 of flexing retaining elements 422 can be formed to generally the shape of the barrel of syringe 600 (that is, generally in the shape of a cylinder or a portion thereof). Preferably, the contact of syringe flange 620 with flexing retaining elements 422 is generally symmetrical. As described above, generally symmetrical loading of flange 620 or other abutment surface on syringe 600 reduces or prevents bending moments on syringe 600.

Adapter 400 preferably further includes a plunger extension carriage 700 that can form a removable connection with piston 550 of injector 500. In that regard, carriage 700 includes a plunger interface or adapter on a rear section thereof that cooperates with piston 550 to form a removable connection therewith. As known in the art, many types of interfaces or connectors can be used to connect an injector piston to a plunger or adapter. The plunger interface of carriage 700 operates generally in the manner of one or more of the plunger/piston interfaces disclosed in PCT Publication No. WO 01/37903, assigned to the assignee of the present invention, the disclosure of which is incorporated herein by reference.

Carriage 700 is maintained in a rearward position within cradle 402 by abutment with a biased (for example, spring-loaded) abutment member 490 (for example, a spring-loaded ball) disposed in passage 492 formed in cradle 400 (see FIG. 5). As piston 550 is advanced in a forward direction, a surface 554 of piston 550 contacts carriage 700 at a rear surface thereof. Further forward motion of piston 550 causes carriage 700 to move forward of (i.e., to overcome the biasing force of) abutment member 490 until biased contact member 710 contacts the rearward surface of flange 642. Preferably the forward surface of contact member 710 is of a sufficient diameter that it will abut a rearward surface of flange 642 even if a hole or passage is formed in the rear surface thereof as is the case with many types of syringes. As piston 550 is advanced, contact member 710 moves rearward causing biased (for example, spring-loaded via spring 557) pin 556 to move rearward. Eventually, a sensor 558 senses the rearward movement of pin 556 relative to sensor 558 and the control system of injector 500 can be alerted that carriage 700 is connected or near connection to plunger extension 640.

In that regard, carriage 700 further includes a plunger extension connector to form a releasable connection with plunger extension 640 of syringe 600. In the embodiment of FIG. 5-7, carriage 700 includes two capture members 720 that flex radially outward to form a releasable connection with flange 642 of plunger extension 640. In that regard, a preferably angled surface 722 of each capture member 720 contacts the rear surface of flange 642 as piston 550 is advanced, causing capture members 720 to flex radially outward. After piston 550 advances a sufficient distance, capture members 720 "snap back" to seat flange 642 in seatings 724 formed in each of capture members 720. In one embodiment, sensor 558 alerts the control system of injector 500 a known amount of time before flange 642 is seated in seatings 724 so that the control system stops advancement of piston 550 after a secure connection is made between carriage 700 and plunger extension flange 642, but before piston 550 is advanced to a degree to cause injection of fluid from the interior of syringe 600.

Preferably, the axial force required to engage capture members 720 with flange 642 is less than the static friction of syringe plunger 610 within syringe 600 so that engagement of capture members 720 with flange 642 does not cause movement of syringe plunger 610.

Seating 724 of each capture member 720 is preferably oriented so that the capture members 720 are disengaged when a user lifts syringe 600 upward from adapter 400. Once flange 642 is removed from connection with capture members 720 and biased contact member 710 (biased, for example, via spring 712) is removed from contact with the rearward surface of flange 642, biased contact member 710 and biases sensing pin 556 preferably return to forward/disengaged positions as illustrated in FIG. 7.

Carriage 700 slides within cradle 400 on guides 414 that are seated within channels 732 formed in each housing member 730 of carriage 700. As illustrated, for example, in FIGS. 6A through 6C carriage 700 can be formed by connection of housing members 730 via fasteners 734 (for example, screws). Capture members 720 can be formed as part of a subassembly 726 that is attachable to housing members 730 via fasteners 728 (for example, screws).

Piston 550 also includes retractable pins (corresponding pins 552' on piston 550' are shown extended to form a mating connection with plunger 342 of syringe 300 in the upper half of FIG. 7) that form an abutting connection with one or more ledges, flanges or grooves 740 formed at a known axial position around the interior circumference of syringe carriage 700 when piston 550 is retracted to draw carriage 700 rearward. Preferably, groove(s) 740 are formed around a sufficient percentage of the inner circumference of housing members 730, such that the relative radial orientations of piston 550 and carriage 700 (that is, the degree to which piston 550 is rotated about its axis relative to carriage 700) is irrelevant to whether a connection between the retractable pins of piston 550 and groove(s) 740 can be made. In the embodiment of FIG. 5-7, groove 740 extends completely around the inner circumference of carriage 700. Capture members 720 maintain a connection with flange 642 to draw plunger extension 640 rearward when piston 550 is retracted. As piston 550 is retracted, capture members 720 maintain connection with plunger extension 640 to retrace plunger extension 640.

FIGS. 8A through 8D illustrate another embodiment of an adapter 400a of the present invention that is similar in operation in many respects to adapter 400 of FIGS. 5 through 7. Like components of adapter 400a are numbered similarly to corresponding components of adapter 400 with addition of the designation "a". The operation of such like components is as described for adapter 400, unless otherwise set forth.

Like adapter, 400, adapter 400a includes a syringe cradle 402a. Adapter 400a is attachable to an injector such as injector 500 via a rear adapter or connector section 450a, including an attachment flange 460a as described above for connector section 450 of adapter 400. Syringe cradle 402a provides space for attachment of syringe 1000, which includes an extending plunger pushrod 1040, to injector 500 or to another injector. Syringe cradle 400a includes two generally, axially-oriented, members 404a and 406a which are connected at the rear thereof via a rear transverse member 410a oriented generally perpendicular to the axis of adapter 400a.

Adapter 400a further includes a syringe interface or adapter 420a at a forward end thereof between axially extending members 404a and 406a. Syringe adapter or interface 420a can be made removable/interchangeable as described above for syringe adapters 250 and 350. Syringe interface 420a is permanently affixed to adapter 400a in the embodiments of FIGS. 8A-8E. Different syringe interfaces can be attached to injector 500 by removing adapter 400a and attaching another adapter with a different syringe interface or adapter.

Syringe interface 420a also includes at least one, and preferably at least two, retaining members or elements 422a disposed within grooves or slots 430a on each lateral side of syringe interface 420. Similar to flexible retaining elements 422, retaining elements 422a can be shaped to conform to the shape of the barrel of syringe 1000. Also similar to flexible retaining elements 422, biased retaining elements 422a permit syringe 1000 to be loaded radially from above into syringe interface 420a by flexing radially outward and snapping back into place after syringe 1000 has been loaded. Unlike flexible retaining elements 422, however, retaining elements 422a are biased by a spring 423a (see, FIGS. 8B and 8E) and need not be formed from a resilient or flexible material.

Syringe 1000 is constrained in the radial direction by retaining elements 422a. Adapter 400a also includes slots, flanges or abutments 432a to the rear of slots 430a to retain syringe 1000 in an axial direction. In that regard, when syringe 1000 is lowered into adapter 400a, syringe flange 1020 abuts a rearward facing surface of slots 432a, preventing forward axial motion of syringe 1000. Preferably, the contact of syringe flange 1020 with slots 432a is generally symmetrical, as described above, to prevent bending moments on syringe 1000. Providing separate slots 432a to retain syringe flange 1020 removes axial loads from retaining elements 422a as compared to flexible retaining elements 422 of adapter 400. Retaining syringe flange 1020 in slot 432a, separate from retaining elements 422a, can result in a reduction of force required to remove syringe 1000 from adapter 400a. In that regard, an injector such as injector 500 places some axial load upon a syringe after an injection is completed.

Adapter 400a preferably further includes plunger extension carriage 700 as described above that can form a removable connection with, for example, piston 550 of injector 500. Capture members 720 of carriage 700 flex radially outward to form a releasable connection with flange 1042 of plunger extension 1040 as described above.

Adapter 400a also further includes a forward support member 800 extending forward from syringe interface 420a. Support member 800 preferably includes or has attached thereto a heater 900 suitable to heat fluid within syringe 1000. As known in the art, heating fluid to be injected into a patient to a temperature near the body temperature of the patient can make the injection more comfortable for the patient. In the embodiment of FIG. 8A through 8E, heater 900 includes a downward extending base 910 that seats in a seating passage 810 of support member 800. A conduit or cable 920 for electrical connection extends from base 910. Heater 900 further includes side elements or contact members 930 and 930' which preferably generally conform to and contact the outer wall of the barrel of syringe 1000 along at least a portion of the length of the barrel when syringe 1000 is attached to adapter 400a to conduct heat through the barrel of syringe 1000 to the fluid therein. As clear to one skilled in the art, the amount of contact required between elements 930 and 930' and the energy required to be supplied thereto can be readily determined for a given desired fluid temperature using thermodynamic principles well known in the art. Elements 930 and 930' can, for example, flex outward when syringe 1000 is placed into adapter 400a from above and bias against the barrel of syringe 1000 once syringe 1000 is seated in adapter 400a and heater 900.

Support member 800 preferably further includes a passage 840 toward the rear of support member 800 in the vicinity of syringe interface 420a. After syringe 1000 is seated in syringe interface 420a, removal of the syringe is facilitate by application of an upward force to syringe 1000 through passage 840. Passage 840 is preferably positioned near syringe interface 420a to reduce or minimize torque upon the syringe induced by application of force to a syringe through passage 840. Without limitation, a representative example of a syringe suitable for use with adapter 400a is the 150 mL prefilled syringe available from Daiichi of Tokyo, Japan.

In the embodiment of FIGS. 8A-8E, support 800 extends forward along the entire length of syringe 1000. In this embodiment, support 800 can also include a radially inward extending flange 850 on a forward end thereof to contact a forward surface of syringe 1000.

Although the present invention has been described in detail in connection with the above embodiments and/or examples, it should be understood that such detail is illustrative and not restrictive, and that those skilled in the art can make variations without departing from the invention. The scope of the invention is indicated by the following claims rather than by the foregoing description. All changes and variations that come within the meaning and range of equivalency of the claims are to be embraced within their scope.

What is claimed is:

1. A syringe interface for connecting a syringe comprising a flange with a forward facing abutment surface and a plunger movably disposed therein to an injector comprising a drive member, the syringe interface comprising:
    a U-shaped top opening into which the syringe can be loaded;
    a groove extending within the U-shaped top opening;
    a first retaining member positioned within the groove at one side of the U-shaped opening; and
    a second retaining member positioned within the groove at a second side of the U-shaped opening, the first retaining member and the second retaining member abutting the forward facing abutment surface of the syringe flange generally symmetrically,
    wherein each of the first retaining member and the second retaining member comprises a radially inward extending member disposed within the groove and that moves radially outward when contacted by the syringe during loading of the syringe into the syringe interface and returns to a radially inward position once the syringe is loaded within the syringe interface.

2. The syringe interface of claim 1 wherein the radially inward extending member returns to a radially inward position after loading of the syringe in a manner that causes audible feedback to inform a user that the syringe is properly seated within the syringe interface.

3. The syringe interface of claim 1, further comprising a carriage slidably connected therein comprising a plunger connector to form a releasable connection with the plunger of the syringe and the drive member of the injector.

4. The syringe interface of claim 3 wherein the carriage slides within a cradle section of the syringe interface positioned in front of the injector connector.

5. The syringe interface of claim 3 wherein the plunger connector comprises a plurality of flexing capture members extending in the axial direction, wherein the plurality of flexing capture members flex radially outward to connect to a flange on the rear of the syringe plunger when the carriage is moved forward within the syringe interface.

6. The syringe interface of claim 5 wherein the carriage further comprises a drive member connector to form a releasable connection with the drive member.

7. The syringe interface of claim 6 wherein the drive member connector comprises at least one abutment flange to form an abutting connection with at least one radially projecting member of the drive member.

8. The syringe interface of claim 7 wherein the drive member connector can be connected to the drive member regardless of the orientation of the carriage about its axis relative to the drive member.

9. The syringe interface of claim 1, further comprising a connector on a rear portion thereof to connect the syringe interface to the injector.

10. An injector system comprising the syringe interface of claim 1.

11. A method of attaching a syringe comprising a flange and a plunger movably disposed therein to the syringe interface of claim 1, the method comprising:
    loading the syringe into the top opening of the syringe interface; and
    engaging the syringe flange with the first and second retaining members of the syringe interface.

12. The method of claim 11, further comprising:
    engaging the syringe plunger with the plunger connector of the syringe interface.

13. A syringe interface for connecting a syringe comprising a flange with a forward facing abutment surface and a plunger movably disposed therein to an injector comprising a drive member, the syringe interface comprising:
    a cradle member;
    at least one engagement member adapted to abut the forward facing abutment surface of the syringe flange; and
    a carriage slidably disposed within the cradle, the carriage comprising a plunger connector to form a releasable connection with the syringe plunger and the drive member of the injector, the plunger connector comprising a plurality of flexing capture members extending in the axial direction, wherein the plurality of flexing capture members flex radially outward to connect to a flange on the rear of the syringe plunger when the carriage is moved forward within the syringe interface, wherein the flexible capture members each terminate with an inwardly angled surface.

14. The syringe interface of claim 13, further comprising an injector connector on a rear portion thereof to connect the syringe interface to the injector.

15. An injector system comprising the syringe interface of claim 13.

16. A syringe adapter for use with a syringe, the syringe including a radially extending flange with a forward facing abutment surface, the adapter including a U-shaped top opening into which the syringe can be loaded,
    a groove extending within the U-shaped top opening;
    a first retaining member positioned within the groove one side of the U-shaped opening and a second retaining member positioned within the groove a second side of the U-shaped opening, the first retaining member and the second retaining member abutting the forward facing abutment surface of the syringe flange generally symmetrically, wherein at least one of the first retaining member and the second retaining member includes a flexible, radially inward extending member disposed within the groove and that flexes radially outward when contacted by the syringe during loading of the syringe into the adapter and returns to a radially inward position once the syringe is loaded within the adapter.

17. The adapter of claim 16 wherein each of the first retaining member and the second retaining member include a flexible, radially inward extending member disposed within the groove and that flexes radially outward when contacted by the syringe during loading of the syringe into the adapter and returns to a radially inward position once the syringe is loaded within the adapter.

18. The adapter of claim 16 wherein the radially inward extending member returns to a radially inward position after loading of the syringe in a manner that causes audible feedback to inform a user that the syringe is properly seated within the syringe adapter.

19. The adapter of claim 16 further including a third retaining member positioned to the rear of the first retaining member and the second retaining member, the third retaining member having generally the same shape as the rearward end of the syringe, the third retaining member being adapted to abut the rearward end of the syringe after the syringe has been loaded into the syringe adapter and the third retaining member has been placed in a closed position to reduce distortion of the shape of the syringe during an injection procedure.

20. The adapter of claim 16, further comprising an injector connector on a rearward end thereof to connect the adapter to a syringe interface of an injector.

21. The adapter of claim 20, further comprising a carriage slidably connected therein, the carriage comprising a plunger connector to form a releasable connection with a plunger of the syringe.

22. An injector system comprising a powered injector, the powered injector including at least a first drive member for pressurizing a fluid within a first syringe, a cradle extending forward of a first opening in the injector through which the drive member communicates with the interior of the first syringe, at least a first syringe adapter retention mechanism on a forward end of the cradle, and a first adapter for attaching the first syringe to the injector, the first adapter including a releasable attachment mechanism for releasably attaching the first adapter to the first adapter retention mechanism, the first adapter further including a top opening into which the first syringe can be loaded, a first retaining member positioned on one side of the opening and a second retaining member positioned on a second side of the opening, the first retaining member and the second retaining member abutting the forward facing abutment surface generally symmetrically, each of the first retaining member and the second retaining member includes a flexible, radially inward extending member that flexes radially outward when contacted by the first syringe during loading of the first syringe into the adapter and returns to a radially inward position once the first syringe is loaded within the adapter.

23. The injector of claim 22 wherein the radially inward extending member returns to a radially inward position after loading of the syringe in a manner that causes audible feedback to a user to let the user know the syringe is properly seated within the syringe adapter.

24. The injector of claim 22, further comprising a third retaining member positioned to the rear of the first retaining member and the second retaining member, the third retaining member having generally the same shape as the rearward end of the syringe, the third retaining member being adapted to abut the rearward end of the syringe after the syringe has been loaded into the syringe adapter and the third retaining member has been placed in a closed position to reduce distortion of the shape of the syringe during an injection procedure.

25. An injector system comprising a powered injector including at least a first drive member for pressurizing a fluid within a first syringe and a second drive member for pressurizing fluid within a second syringe, a cradle extending forward of a first opening in the injector through which the first drive member communicates with the interior of the first syringe and a second opening in the injector through which the second drive member communicates with the interior of the second syringe, a first syringe adapter retention mechanism on a forward end of the cradle, a second syringe adapter retention mechanism on a forward end of the cradle, the injector system further including a first adapter for attaching the first syringe to the injector, and a second adapter for attaching the second syringe to the injector, at least the first adapter including a releasable attachment mechanism for releasably attaching the first adapter to the first adapter retention mechanism, the first adapter including a top opening into which the syringe can be loaded, a first retaining member being positioned on one side of the opening and a second retaining member being positioned on a second side of the opening, the first retaining member and the second retaining member abutting the forward facing abutment surface on the first syringe generally symmetrically, each of the first retaining member and the second retaining member includes a flexible, radially inward extending member that flexes radially outward when contacted by the first syringe during loading of the first syringe into the adapter and returns to a radially inward position once the first syringe is loaded within the adapter.

* * * * *

UNITED STATES PATENT AND TRADEMARK OFFICE
CERTIFICATE OF CORRECTION

| | | |
|---|---|---|
| PATENT NO. | : 7,691,085 B2 | Page 1 of 1 |
| APPLICATION NO. | : 10/295297 | |
| DATED | : April 6, 2010 | |
| INVENTOR(S) | : Dedig et al. | |

It is certified that error appears in the above-identified patent and that said Letters Patent is hereby corrected as shown below:

Title page, under "Primary Examiner", in Column 2, Line 1, delete "Nicholas A" and insert -- Nicholas D --, therefor.

IN THE SPECIFICATION

In Column 2, Line 31, delete "injector," and insert -- injector. --, therefor.

In Column 5, Line 39, delete "injector" and insert -- injector. --, therefor.

In Column 11, Line 22, delete "FIG." and insert -- FIGS. --, therefor.

Signed and Sealed this
Eleventh Day of September, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,691,085 B2 | Page 1 of 2 |
| APPLICATION NO. | : 10/295297 | |
| DATED | : April 6, 2010 | |
| INVENTOR(S) | : Dedig et al. | |

It is certified that error appears in the above-identified patent and that said Letters Patent is hereby corrected as shown below:

Title page, under "Primary Examiner", in Column 2, Line 1, delete "Nicholas A" and insert
-- Nicholas D --, therefor.

IN THE SPECIFICATION

In Column 2, Line 31, delete "injector," and insert -- injector. --, therefor.

In Column 5, Line 39, delete "injector" and insert -- injector. --, therefor.

In Column 11, Line 22, delete "FIG." and insert -- FIGS. --, therefor.

IN THE CLAIMS

In Column 13, Lines 36-37, in Claim 2, delete "that causes audible feedback." and insert
-- that causes an audible feedback. --, therefor.

In Column 14, Line 9, in Claim 12, delete "with the plunger" and insert -- with a plunger --, therefor.

In Column 14, Lines 61-62, in Claim 18, delete "that causes audible feedback" and insert
-- that causes an audible feedback --, therefor.

In Column 14, Line 67 – Column 15, Lines 1-2, in Claim 19, delete "the rearward end of the syringe"
and insert -- a rearward end of the syringe --, therefor.

In Column 15, line 17, in Claim 22, delete "communicates with the interior" and insert
-- communicates with an interior --, therefor.

This certificate supersedes the Certificate of Correction issued September 11, 2012.

Signed and Sealed this
Thirtieth Day of October, 2012

David J. Kappos
*Director of the United States Patent and Trademark Office*

CERTIFICATE OF CORRECTION (continued)

IN THE CLAIMS:

In Column 15, Lines 27-28, in Claim 22, delete "abutting the forward facing" and insert -- abutting a forward facing --, therefor.

In Column 15, Lines 38-39, in Claim 23, delete "causes audible feedback" and insert -- causes an audible feedback --, therefor.

In Column 16, Lines 4-5, in Claim 24, delete "the rearward end of the syringe" and insert -- a rearward end of the syringe --, therefor.

In Column 16, Line 6, in Claim 24, delete "the rearward end of the syringe" and insert -- a rearward end of the syringe --, therefor.

In Column 16, Line 15, in Claim 25, delete "the interior" and insert -- an interior --, therefor.

In Column 16, Line 17, in Claim 25, delete "the interior" and insert -- an interior --, therefor.

In Column 16, Line 27, in Claim 25, delete "the syringe" and insert -- the first syringe --, therefor.

In Column 16, Claim 25, Line 28, delete "the opening" and insert -- the first opening --, therefor.

In Column 16, Claim 25, Lines 29-30, delete "the opening" and insert -- the first opening --, therefor.

In Column 16, Line 31, in Claim 25, delete "the forward facing abutment surface on the first syringe" and insert -- a forward facing abutment surface on the first syringe --, therefor.